United States Patent [19]

Kaufman et al.

[11] Patent Number: 4,912,040

[45] Date of Patent: Mar. 27, 1990

[54] EUCARYOTIC EXPRESSION SYSTEM

[75] Inventors: Randal J. Kaufman, Boston; Andrew Dorner, Melrose, both of Mass.

[73] Assignee: Genetics Institute, Inc., Cambridge, Mass.

[21] Appl. No.: 10,351

[22] Filed: Feb. 3, 1987

Related U.S. Application Data

[63] Continuation-in-part of Ser. No. 931,381, Nov. 14, 1986, abandoned.

[51] Int. Cl.[4] .................. C12P 21/00; C12P 21/02; C12P 21/04; C12P 19/34; C12N 15/00; C12N 5/00; C12N 5/02; C12N 1/20; C07H 21/04

[52] U.S. Cl. .................. 435/69.6; 435/69.1; 435/91; 435/172.1; 435/172.3; 435/240.1; 435/240.2; 435/240.4; 435/252.3; 435/320; 536/27; 935/11; 935/32; 935/34; 935/61; 935/67; 935/68; 935/69; 935/70

[58] Field of Search .............. 435/68, 74, 71, 91, 435/172.1, 172.3, 240.1, 240.2, 240.4, 253, 254, 255, 256, 320, 252.3, 252.31-252.35; 530/387; 536/27; 935/11, 22, 32, 61, 67, 68, 69, 70, 34

[56] References Cited

PUBLICATIONS

Izant et al.; Science 229: 346 (1985).
Lee et al.: J. Biolo. Chem. 258: 597 (1983).
Lin et al.: Mol. Cell. Biol. 6: 1235 (1986).
Attenello et al.; Science 226: 187 (1984).
Toole et al.; Nature 312: 342 (1984).

*Primary Examiner*—James Martinell
*Attorney, Agent, or Firm*—David L. Berstein; Bruce M. Eisen

[57] ABSTRACT

This invention provides vectors, improved host cells and improved methods for producing a heterologous protein by culturing an improved eucaryotic host cell of this invention transformed or transfected with a vector capable of directing the expression of the heterologous protein. The preferred improved host cell of this invention is a mammalian host cell containing and capable of expressing an anti-sense GRP78 DNA sequence.

7 Claims, No Drawings

EUCARYOTIC EXPRESSION SYSTEM

This application is a continuation in part of U.S. Ser. No. 931,381, filed 14 Nov. 1986 (now abandoned).

BACKGROUND OF THE INVENTION

This invention relates to improvements in the expression and secretion of heterologous proteins from eucaryotic cells. Complete citations for references cited herein are set forth immediately preceding the claims.

The information which determines the destiny of a secreted protein is contained in its primary structure, and much of this information may involve dictating appropriate post-translational modification and correct conformation. The steps in the exocytotic pathway of the processing and transit of membranespanning and secretory proteins in mammalian cells have been described (for reviews see Farquhar Ann Rev Cell Biol 1985; Kornfeld & Kornfeld Ann Rev Biochem 1985). A large body of work has shown that proteins destined for the cell surface are first cotranslationally translocated into the lumen of the endoplasmic reticulum (ER) mediated by a signal sequence at or near the amino terminus of the nascent chain (Blobel & Dobberstein J. Cell Biol 1975; Walter et al Cell 1984). Inside the endoplasmic reticulum the signal sequence is usually removed and a high mannose oligosaccharide core unit is transferred to a sparagine residues located in the sequence Asn-X-Ser/Thr where X can be any amino acid, except perhaps proline. This N-linked core glycosylation occurs cotranslationally and it appears that the efficiency of glycosylation is dependent on the presentation of an appropriate conformation of the peptide chain as it enters the endoplasmic reticulum. Potential N-linked glycosylation sites may no longer be accessible after the protein has folded (Kornfeld & Kornfeld).

Proteins move from the endoplasmic reticulum to the Golgi apparatus where modifications such as sulfation and processing of the high mannose oligosaccharide chain to a complex type occurs and the proteins are directed to their proper destinations (Dunphy & Rothman Cell 1985). The movement from the ER to the Golgi has been identified as the rate limiting step in intracellular transport (Lodish et al. Nature 1983; Fitting & Kabat JBC 1982 J. Cell Biol 1985). Few proteins resident in the ER have been extensively studied for their interaction with secretory proteins transiting that compartment.

Environmental stresses such as heat shock induce the synthesis in prokaryotic and eukaryotic cells of a set of highly conserved heat shock proteins. (Schlesinger, J. Cell Biol 1986). hsp70 is the most abundant of these induced proteins. Proteins related to hsp70 are found in unstressed mammalian cells. There are three main members of the mammalian hsp70-like group of proteins: hsp70, hsc70, and GRP78 (Pelham Cell 1986) Following heat shock, synthesis of hsp70 is induced and the protein migrates to the nucleus where it is found in tight association with nucleoli. hsp70 can be released from this association by the addition of ATP in. vitro. It has been hypothesized that hsp70 disaggregates heat damaged proteins by an ATP dependent mechanism to facilitate recovery from heat shock (Lewis & Pelham EMBO J 1985). hsc70 is found at high basal levels in growing cells and is only slightly heat inducible (Pelham Cell 1986). hsc70 has recently been identified as "uncoating ATPase", a constitutively expressed enzyme that releases clathrin triskelions from coated vesicles in an ATP dependent reaction (Chappell et al Cell 1986, Ungewickell EMBO J 1985).

GRP78 was initially reported to be one of two proteins whose synthesis was induced by glucose starvation in chick fibroblasts (Shiu et al Proc. Natl. Acad. Sci. U.S.A. Its synthesis can also be induced by inhibitors of N-linked glycosylation such as tunicamycin, glucosamine or 2-deoxyglucose (Olden et al Proc. Natl. Acad. Sci. U.S.A 1979, Pouyssegur et al Cell 1977). GRP78 is not heat inducible and its basal level is high in secreting cells. Recently it has been shown that GRP78 is similar if not identical to immunoglobulin heavy chain binding protein (BiP) (Munro and Pelham Cell 1986). GRP78 is therefore also referred to hereinafter as BiP/GRP78 or simply, BiP. BiP was first described for its association with immunoglobulin heavy chains in pre-B cells (Haas and Wable Nature 1983). BiP transiently complexes with immunoglobulin heavy chain in the endoplasmic reticulum of secreting hybridomas. When assembly with light chains occurs BiP dissociates from the complex. In the absence of light chains BiP remains associated with heavy chains and this complex is not transported from the endoplasmic reticulum to the Golgi apparatus (Bole et al J. Cell Biol 1986). These subcellular fractionation studies showed that BiP is predominantly localized to the endoplasmic reticulum. The heavy chain-Bip complex can be dissociated in the presence of ATP suggesting a functional analogy with the hsp70 complex in heat shocked nucleoli. (Munro & Pelham Cell 1986).

We believe that BiP/GRP78 may associate in secreting cells with underglycosylated or improperly folded proteins in the endoplasmic reticulum and help clear them in analogy to the hypothesized role of hsp70 in the nucleus (Pelham Cell 1986). Such a function is consistent with the induction of increased levels of GRP78 synthesis under conditions which disrupt N-linked glycosylation. Recent studies on abberant proteins which fail to transit out of the ER have been interpreted to show that BiP binds to them in the ER although the identity of grp78 and BiP was disputed (Gething et al Cell 1986; Sharma et al EMBO J 1985) and the extent and degree of such binding was not specifically characterized. BiP/GRP78 may also associate with partially assembled proteins and retain them in the ER until assembly and processing is complete as is the case for the processing of immunoglobulin heavy chain (Bole et al J Cell Biol 1986).

Independent of the research on BiP mentioned above, we have conducted extensive research on the production of glycoproteins, including Factor VIII, in genetically engineered host cells. In the course of this research we have surprisingly found that a significant proportion of Factor VIII produced in vitro, e.g. in CHO cells, is not secreted into the cell culture medium. We have now surprisingly found that secretion levels for Factor VIII and other glycoproteins can be decreased by providing higher intracellular levels of BiP and can be increased by reducing the intracellular BiP level.

SUMMARY OF THE INVENTION

This invention provides an anti-sense expression vector capable of directing the transcription of mRNA complementary to mRNA encoding GRP78 protein (BiP). The anti-sense expression vector thus directs the transcription of "anti-sense" mRNA which is capable of hybridizing to part or all of the endogenous GRP78/BiP-encoding mRNA, thereby preventing translation of GRP78/BiP mRNA in a host cell transformed or transfected with the expression vector of this invention. The anti-sense expression vector comprises a DNA sequence encoding part or all of a GRP78 protein or an expression control sequence thereof, operatively linked in reverse orientation to an expression control sequence permitting transcription of the anti-sense mRNA. The anti-sense mRNA, and thus the corresponding DNA in the anti-sense expression vector, (i) need not be full-length, i.e. may contain fewer bases or base pairs than the host cell's BiP-encoding mRNA or DNA, and/or (ii) may be mutagenized or otherwise contain a number of substituted bases or base pairs for naturally occurring ones, so long as the anti-sense mRNA hybridizes to a sufficient portion of the host cell's GRP78/BiP mRNA to prevent or significantly reduce GRP78/BiP mRNA translation. The anti-sense expression vector may also contain one or more amplifiable markers permitting the amplification of gene copy number by conventional techniques, one or more selectable markers, and other elements heretofore generally known in the art to be useful in expression vectors, as disclosed in greater detail below.

Suitable anti-sense expression vectors, as are described in greater detail herein, may be synthesized by techniques well known in the art. The components of the vectors such as bacterial replicons, selection genes, amplifiable markers, enhancers, promoters, and the like may be obtained from natural sources or synthesized by known procedures. See Kaufman et al., 1982, *J. Mol. Biol.*, 159:601-621; Kaufman, 1985, *Proc. Natl. Acad. Sci.* 82:689-693. The DNA sequence encoding the BiP antisense mRNA may be obtained or synthesized as described hereinafter.

This invention further encompasses an improved eucaryotic host cell for expressing a heterologous protein such as Factor VIII or analogs thereof; t-PA or variants thereof; von Willebrand Factor (VWF); erythropoietin; lymphokines such as GM-CSF, other CSFs, I1-2, I1-3; etc. The improved host cell comprises a host cell transformed or transfected with an anti-sense expression vector of this invention. The improved host cell may be a bacterial, yeast, fungal, plant, insect or mammalian cell or cell line, and is preferably a mammalian cell or cell line.

Established cell lines, including transformed cell lines, are suitable as hosts. Normal diploid cells, cell strains derived from in vitro culture of primary tissue, as well as primary explants (including relatively undifferentiated cells such as hematopoetic stem cells) are also suitable. Candidate cells need not be genotypically deficient in a selection gene so long as the selection gene is dominantly acting.

The host cells preferably will be established mammalian cell lines. For stable integration of vector DNA into chromosomal DNA, and for subsequent amplification of the integrated vector DNA, both by conventional methods, CHO (Chinese Hamster Ovary) cells are presently preferred. Alternatively, vector DNA may include all or part of the bovine papilloma virus genome (Lusky et al., 1984, Cell 36:391-401) and be carried in cell lines such as C127 mouse cells as a stable episomal element. Other usable mammalian cell lines include HeLA, COS-1 monkey cells, melanoma cell lines such as Bowes cells, mouse L-929 cells, 3T3 lines derived from Swiss, Balb-c or NIH mice, BHK or HAK hamster cell lines and the like.

The improved host cell may further be transformed or transfected with an expression vector capable of directing the expression of the desired protein. Suitable vectors for the expression of a large number of diverse proteins are known in the art and are either publicly available or may be synthesized by purely conventional techniques. Vectors containing DNA encoding the following proteins, for example, have been deposited with the American Type Culture Collection (ATCC) of Rockville, MD: Factor VIII (pSP64-VIII, ATCC No. 39812); a Factor VIII analog, "LA", lacking 581 amino acids (pDGR-2, ATCC No. 53100); t-PA and analogs thereof (see co-pending U.S. application Ser. No. 882,051); VWF (pMT2-VWF, ATCC No. 67122); EPO (pRK1-4, ATCC No. 39940; pdBPVMMTneo 342-12 (BPV-type vector) ATCC No. 37224); and GM-CSF (pCSF-1, ATCC No. 39754).

An improved method is thus provided for producing a heterlogous protein, e.g. Factor VIII, etc., by culturing a eucaryotic host cell transformed with a vector capable of directing the expression of a heterologous protein. The improvement involves using as the host cell a host cell transformed or transfected with an anti-sense GRP78/BiP vector of this invention.

Stable transformants are then screened for decreased expression of BiP and/or expression of the heterologous protein by standard immunological or enzymatic assays. The presence of anti-sense mRNA and/or DNA encoding the heterologous protein may be detected by standard procedures such as Northern or Southern blotting respectively. Transient expression of the anti-sense vector and/or the DNA encoding the heterologous protein during the several days after introduction of the respective vectors(s) into COS-1 monkey cells is measured without selection by activity or immunological assay of the proteins in the culture medium.

Following expression of the DNA encoding the heterologous protein, the protein so produced may be recovered, purified, and/or characterized, all by known methods.

This invention also encompasses a "sense" GRP78/BiP expression vector which comprises a DNA sequence encoding GRP78/BiP operatively linked to an expression control sequence. Construction of an exemplary GRP78/BiP expression vector is described in detail below, but it should be understood that other BiP expression vectors may be readily prepared by purely conventional techniques using a GRP78/BiP-encoding DNA sequence and readily available or synthesizable components, as is true for other exemplary vectors of this invention described hereinafter.

This invention also encompasses a eucaryotic host cell, as described above, but which is transformed or transfected with a GRP78/BiP expression vector. Such an engineered host cell may be further transformed with an expression vector capable of directing the transcription of a heterologous protein, also as described above. The resultant cell may then be cultured in an improved method for producing the heterologous protein, wherein improperly glycosylated or folded heterologous protein is not secreted into the culture medium, but is instead retained within the host cell by virtue of association with intracellular BiP.

DETAILED DESCRIPTION OF THE INVENTION

We have examined the role of BiP/GRP78 in the processing and secretion of a variety of proteins, including human factor VIII (FVIII), human tissue plasminogen activator (tPA) and human von Willebrand Factor (vWF) in host cells such as stable Chinese hamster ovary (CHO) cell lines. FVIII is synthesized as a single chain precursor of about 250 kd and subsequently processed to a "heavy chain" of about 200 kd and a "light chain" doublet of about 80 kd. FVIII has a plethora of potential N-linked glycosylation sites. Twenty of the twenty-five sites are located within the middle one-third of the molecule which has been defined as the B domain. (Toole et al Nature 1984) Deletion of this domain to produce the "LA" variant of FVIII results in higher levels of FVIII secretion (Toole et al Proc. Natl. Acad. Sci. U.S.A. 1986). tPa has a molecular weight of about 68,000 kd and contains four potential N-linked glycosylation sites of which three are typically occupied (Pohl et al. Biochem 1984). vWF is a large glycoprotein synthesized as an approximately 260,000 kd precursor which forms dimers in the endoplasmic reticulum and is subsequently processed in Golgi and post-Golgi compartments to approximately 100,000 and 220,000 kd forms (Bonthron et al. Nature 1986). These processed forms undergo interdimer disulfide bond formation to form high molecular weight multimers (Wagner & Marder J. Cell Biol 1984).

Our results indicate that the occupancy of N-linked glycosylation sites on a protein plays a role in the extent of BiP association. Underglycosylation of a protein results in increased BiP association and retention inside the cell. This block to secretion may be dependent on expression level. We believe that BiP/GRP78 plays a major role in the processing and transport of secreted glycoproteins.

RESULTS

Association of FVIII and Deleted Form LA with BiP

In order to qualitatively assess the role of BiP/GRP78 in the secretory pathway we examined a variety of stable CHO cell lines by pulse and chase experiments. The time course of association of FVIII and BiP was analyzed by comparing the amount of FVIII which was detected by immunoprecipitation with a monoclonal antibody specific for BiP against that precipitated with a monoclonal specific for FVIII. Following a 1 hour pulse with $^{35}$S methionine roughly 85% of wild-type (wt) FVIII was detected in a complex with BiP as indicated by the amount of FVIII seen in the anti-BiP immunoprecipitation compared to that precipitated by the anti-FVIII monoclonal. Only the 250 kD single chain form was found to be associated with BiP. No processed 80 kD form was precipitated by the anti-Bip monoclonal although it is present in the cells at this time. BiP was observed to migrate slightly faster than the 80 kD doublet.

At the 4 h chase time point processed heavy chain of 200 kD and the 80 kD light chain doublet can be detected in the conditioned medium. Immunoprecipitation of the conditioned medium detected a slight amount of BiP. However there was no associated FVIII observed. Intracellularly the amount of FVIII associated with BiP had decreased to less than 50% as the molecule transits through the cell. At the 20 h chase time point the ratio of BiP-associated to unassociated FVIII changed. The single chain FVIII had begun to degrade as indicated by a smearing of the 250 kD band as analyzed by gel electrophoresis and roughly all of this FVIII which remained in the cell after a long chase was found complexed with BiP. The amount of BiP had increased in the conditioned medium over this time course but an association with secreted FVIII can not be detected. It is worth noting that through the 20 h chase time course the amount of GRP78 inside the cells does not significantly change. It is secreted or released from damaged cells at a low rate and appears to be stable cellular protein with a half life greater than 20 h.

We then examined the association of LA with BiP in a similar time course. LA is a deleted form of FVIII which has only 7 potential N-linked sites compared to 25 on wt FVIII. At the 1 h pulse time point roughly 60% of single chain LA is associated with BiP. Single chain LA appears as a doublet of approximately 150 kd. As with wt FVIII no 80 kd forms are observed to be complexed with BiP.

During the 4 h chase period the association of LA and BiP significantly decreases compared to the earlier time point. Single chain, processed heavy chain which migrates as a smear around 90 kD, and 80 kD light chain doublet can be detected in the 4 h conditioned medium by immunoprecipitation with anti-FVIII monoclonal. Also present in the medium is trace unassociated BiP. At the 20 h chase time point a small amount of LA remains in the cell and the proportion of LA associated with BiP is slight. These experiments indicated that LA exhibits a transient association with BiP inside the cell and, in contrast to wt FVIII, is not retained intracellularly in a complex with BiP. This suggested that the complexity of the wt FVIII glycosylation may influence the degree of BiP association since deletion of the highly glycosylated region in LA produced a protein which was associated with BiP to a lesser degree than wt FVIII. In this regard it is noteworthy that GRP78 is induced to high levels in CHO cells placed under conditions which affect N-linked glycosylation such as glucose starvation or tunicamycin treatment.

THE EFFECT OF TUNICAMYCIN ON THE ASSOCIATION OF LA AND BIP

This observation that a population of wt FVIII molecules remained inside the cell complexed with BiP after long chase while LA displayed a transient association prompted us to test whether disruption of the glycosylation of LA would result in greater association with BiP. To examine this concept, LA producing cells were treated overnight with 10 ug/ml tunicamycin. This treatment inhibits N-linked glycosylation and has been reported to induce increased levels of GRP78 synthesis (Munro and Pelham, 1986). Following a 1 h pulse with $^{35}$S methionine the extracts of untreated or treated cells were immunoprecipitated with anti-FVIII monoclonal or anti-Bip monoclonal. In the absence of tunicamycin, only a small amount of single chain LA at 150 kd was associated with BiP. In the presence of tunicamycin the molecular weight of the LA doublet was reduced and roughly all of this unglycosylated LA was now associated with BiP. Thus disruption of the glycosylation of LA under conditions which should induce increased levels of GRP78 results in increased association with BiP compared to normally glycosylated LA. This suggested that improper glycosylation of FVIII might influence its association with BiP.

Of particular interest is the detection of a protein induced by tunicamycin treatment which comigrates with the protein identified as BiP by immunoprecipitation with the anti-BiP monoclonal. The molecular weight of BiP does not change following tunicamycin treatment indicating it is not normally N-linked glycosylated.

ASSOCIATION OF VWF WITH BIP

It was possible that the CHO cells were deficient in some aspect of the secretory pathway and so could not properly process a complex glycoprotein. To explore this we examined the processing of vWF in a stable CHO line in a pulse and chase experiment. The precursor form of vWF has 17 N-linked glycosylation sites spread along the molecule. At the 1 h pulse time point the 260 Kda VWF precursor protein is observed inside CHO cells. Roughly 20% of this protein is found complexed with BiP. VWF is efficiently and rapidly secreted such that at the 4 h chase point approximately 90% of the 260 kda precursor is gone from the cell extract and the conditioned medium contains the processed forms of 275 and 220 kD. These processed forms are not observed intracellularly to any significant degree, consistent with observations that this processing of the 260 kda precursor to the 275 and 220 forms occurs rapidly late in the pathway of VWF secretion. At both the 4 h chase and 20 h chase points most of the VWF has been secreted from the cells. Some VWF is still associated with BiP at the 4 h point but little if any BiP-VWF complex is observed at the 20 h chase point. Despite the fact that VWF is a complex glycosylated protein its association with BiP is transient and most of the protein is efficiently secreted from CHO cells. This is in contrast to the situation with wt FVIII and indicates that CHO cells are competent to efficiently secrete a complex glycoprotein.

ASSOCIATION OF TPA WITH BIP

To further analyze the role of glycosylation on protein secretion and Bip association we examined the processing of t-PA in glycosylated and unglycosylated forms in CHO cells. T-PA has 4 potential N-linked glycosylation sites of which 3 are utilized. t-PA appears as a doublet or roughly 68 kD due to variability in the utilization of one of the three glycosylation sites. t-PA3x is genetically engineered mutant in which the three normally utilized N-linked glycosylation sites have been abolished by Asn to Gln codon changes in the canonical recognition site sequences. See International Application No. PCT/US87/00257 (WO 87/04722).

Glycosylated unmodified t-PA (i.e. wild type, "t-PAwt") was efficiently processed and secreted in a high producing CHO cell line, AJ19. At the pulse time point t-PAwt exhibited a slight association with BiP. During the 1 h and 3 h chase periods most of the t-PAwt had been secreted into the medium and little if any association with BiP could be detected intracellularly at these times. Thus, at high intracellular concentrations t-PAwt is correctly processed and secreted without extensive detectable association with BiP.

We next examined the processing of t-PA3x in a low producing cell line, t-PA3x-4, to determine if the absence of N-linked glycosylation in t-PA3x would prevent its efficient secretion, in analogy to our observations with LA. This unglycosylated form of t-PA displays little association with BiP and is efficiently secreted into the medium. The time course of its transit through the cell is similar to that observed for t-PAwt. The majority of the protein has left the cell by the 1 h and 3 h chase time points indicating that t-PA3x does not experience a block in the secretory pathway. Thus, in the absence of glycosylation t-PA remains in a secretion competent form which displays little association with BiP.

However, examination of a high producing t-PA3x cell line, t-PA3x-13, indicated that the association of t-PA3x with BiP is dependent on the expression level. t-PA3x-13 produces roughly 200-fold higher levels of t-PA3x that t-PA3x-4. At high expression levels t-PA3x displays a significant association with BiP in sharp contrast to that observed for the t-PA3x-4 line. The amount of t-PA3x associated with BiP decreases slightly between the pulse time point and the 1 h chase point. However, the amount of t-PA3x found in a complex with BiP remains the same between the 1 h and 3 h chase points. Strikingly, the proportion of t-PA3x associated with BiP increased through the time course such that at the 3 h chase point most of the t-PA3x which remained in the cell was in a complex with BiP. During the time course of this experiment t-PA3x is secreted from the cell but there exists a population of the molecules which are not competent for efficient secretion and apparently enter a stable complex with BiP. This situation is highly reminiscent of that observed with wt FVIII described above. In the case of t-PA3x the efficient of secretion and the extent of BiP association of the unglycosylated protein was influenced by the expression level.

The Effect of Tunicamycin on the Association of t-PA and BiP

Another way to examine unglycosylated forms of t-PA is to inhibit N-linked glycosylation by tunicamycin treatment. Immunofluorescence analysis showed that tunicamycin treatment of t-PAwt-producing cells results in accumulation of t-PA in the endoplasmic reticulum. When the AJ19 cell line is treated with 10 ug/ml tunicamycin for 1 hour the association of the unglycosylated t-PA with BiP is significantly increased compared to t-PAwt. t-PA-BiP complex is detected at the chase time point and there is some inhibition of secretion. Similar treatment of the t-PA3x-13 cell line did not produce an alteration in the amount of t-PA3x associated with BiP compared to untreated cells and the protein is secreted while a fraction of the intracellular t-PA remains associated with BiP. This pattern of protein processing in tunicamycin treated t-PA3x-13 cells looks similar to the untreated time course. This indicated that the influence of tunicamycin treatment on t-PAwt secretion was due to the absence of glycosylation on the molecule itself rather than an indirect effect of the tunicamycin.

It is striking that the t-PAwt treated with tunicamycin profile looks very much like that of t-PA3x at high expression levels. In both cases a similar proportion of the unglycosylated molecules are apparently not competent for efficient secretion and remain in an intracellular complex with BiP. At lower expression levels t-PA3x shows no significant association with BiP. t-PAwt at lower expression levels is affected to a lesser degree by tunicamycin treatment that the high producer cell line. Thus the association of unglycosylated t-PA with BiP is influenced by the intracellular levels of t-PA.

Unglycosylated t-PA appears as doublet in these experiments. t-PA is synthesized with a 12-15 amino acid long propeptide at the amino terminus of the protein (Pennica et al. Nature 1983). Most probably the higher molecular weight band represents the uncleaved pro-t-PA precursor form while the lower band represents the mature form which has been processed to remove the amino terminal propeptide. Since propeptide cleavage occurs in Golgi and post-Golgi compartments and BiP has been localized to the endoplasmic reticulum, only the pro-t-PA precursor form should be present in the same compartment as BiP. Consistent with this interpretations is the observation that only the higher molecular weight species of the doublet is found associated with BiP while only the lower molecular weight species is secreted.

COEXPRESSION OF GRP78 AND FVIII OR LA IN COS CELLS

A cDNA coding sequence for Chinese hamster GRP78 was placed in the expression vector pMT2 which is a derivative of p91023b and this expression vector (pMTGRP78) was cotransfected into COS cells with wt FVIII (pMT2VIII) or LA (pMT2LA) expression vectors to examine the consequences of overexpression of GRP78 on FVIII secretion. The transient expression of FVIII was monitored by assaying the conditioned medium for FVIII activity. Expression of GRP78 was detected by immunoprecipitation with the anti-BiP monoclonal. pMT2 may be obtained from pMT2-vWF (ATCC No. 67122) as described in detail below.

Coexpression of GRP78 and FVIII in COS cells consistently resulted in a 6-10 fold reduction in the levels of FVIII activity in the conditioned medium (Table 1, below). The effect of two different replicating vectors in the same cell is a decrease in the expression of both vectors. To compensate for this phenomenon, FVIII or LA vectors were always cotransfected with pCSF-1. pCSF-1 is an expression vector for GM-CSF which carries similar replication and transcription elements as pMT2 (Wong et al Science 1985). Coexpression of LA and GRP78 in COS cells resulted in a 2-3 fold reduction the levels of LA activity in the medium.

The degree of decrease of activity of LA and wt FVIII are consistent with the degree of association of FVIII and LA with BiP in CHO cells. The heavily glycosylated wt FVIII is more affected by GRP78 expression than LA in the transient COS system and also displays a stronger association with BiP in stable CHO cell lines. This data indicates that high levels of GRP78 can interfere with the secretion of FVIII and is suggestive that BiP and GRP78 are functionally and structurally similar.

EXAMPLES

A. Preparation of GRP78 cDNA

The particular GRP78 cDNA used is a matter of choice. For example, one may use a Chinese hamster cDNA clone p3C5 obtained as described (Lee et al, 1983, J. Biol. Chem. 258:597). Alternatively a rat cDNA clone may be obtained, also as described (Munro & Pelham Cell 1986). Sequence analysis has shown that both of these clones encode the same protein identified as GRP78. At the amino acid level the rat and hamster proteins are 99.4% homologous. Cloning of a functional GRP78 cDNA may be effected using one or more oligonucleotides derived from the published sequence of GRP78 and purely conventional techniques as described by Lee et al. or Munro & Pelham, supra. Alternatively, a cloned rat cDNA may be obtained from Sean Munro, MRC Laboratory of Molecular Biology, Hills Road, Cambridge CB2 2QH, England.

B. Coexpression of Chinese Hamster GRP78 cDNA in Monkey Kidney COS Cells with F(VIII) or LA.

Chinese hamster GRP78 cDNA was placed into a mammalian expression vector pMT2. This vector is a derivative of p91023B and may be obtained by EcoRI digestion of pMT2-vWF, which has been deposited with the American Type Culture Collection under ATCC No. 67122. EcoRI digestion excises the cDNA insert present in pMT2-vWF, yielding pMT2 in linear form which can be ligated and used to transform E. coli HB101 or DH5 to ampicillin resistance. Plasmid pMT2 DNA can then be prepared by conventional methods. The 1962 nucleotide open reading frame encoding hamster GRP78 was excised by PstI and EcoRV digestion. The vector was prepared by EcoRI digestion, the EcoRI ends were filled in using Klenow fragment and then the vector was digested with PstI. The fragment from the hamster clone was ligated into the prepared pMT2 vector, although as indicated previously, other eucaryotic expression vectors may also be used. The resultant plasmid pMTGRP78 contains the adenovirus-VA genes, SV40 replication origin including enhancer, adenovirus major late promoter including tripartite leader and 5' donor splice site, 3' splice acceptor site, GRP78 cDNA insert, DHFR cDNA insert, SV40 early polyadenylation site and pBR322 sequences. pMTGRP78 was used to cotransfect COS-1 cells along with the FVIII expression vectors pMT2VIII or pMT2LA (Toole et al Proc. Natl. Acad. Sci. U.S.A. 1986) using the DEAE dextran procedure (Kaufman Proc. Natl. Acad. Sci. U.S.A. 1985). Conditioned medium was harvested at various times beginning 48 hours post-transfection and assayed for FVIII activity as described (Toole et al Nature 1984). The results of these experiments are summarized in Table I. Previous work has shown that cotransfection of two different expression vectors reduces the level of expression compared to transfection of a single vector. To compensate for this phenomenon the FVIII expression vectors were contransfected with pCSF-1, a previously described vector which expresses GM-CSF (Wong et al Science 1985). pCSF-1 is available from the American Type Culture Collection in E. coli MC1061 as ATCC 39754. The results in Table I show that coexpression of GRP78 and FVIII resulted in roughly six-ten fold reduction in the level of secreted FVIII activity and coexpression of GRP78 and LA resulted in a roughly two-three fold reduction compared to coexpression of FVIII or LA with GM-CSF. Analysis of extracts of COS cells cotransfected with pMTLA and pMTGRP78 or pMT2LA and pCSF-1 and subjected to a pulse/chase $^{35}S$ methionine label showed that in cells expressing pMTGRP78 more LA remained associated with BiP/GRP78 following the chase than was observed in the pCSF-1 cotransfected cells. These results indicated that overexpression of GRP78 prevented the secretion of FVIII by the intracellular association of FVIII and GRP78 and the retention of this complex in the cell. This suggested that otherwise secretion competent FVIII might be trapped inside cells expressing high levels of GRP78 and thus a decrease in GRP78 levels would facilitate the secretion of FVIII and other secretory proteins.

C. Coexpression of Chinese hamster GRP78 antisense cDNA with F(VIII) in Monkey Kidney COS cells.

Chinese hamster GRP78 cDNA was placed into pMT2 in the opposite orientation from that in the above-described expression vector. The 1962 nucleotide open reading frame was excised as follows. The hamster GRP78 clone was digested with EcoRV and a PstI linker was ligated to the blunt EcoRV end. The DNA was then cut with PstI to excise the 1962 bp open reading frame. The vector pMT2 was prepared by digestion with PstI. The fragment from the hamster was ligated into the PstI site of pMT2. The resultant plasmid pMTαB2 was identified by extensive restriction digest mapping to carry the GRP78 cDNA sequences such that the 3' end of the GRP78 cDNA ATCC No. 40387 was closest to the adenovirus major late promoter.

In this orientation transcripts expressed from the adenovirus major late promotor would contain sequence which is the complement of the GRP78 coding sequence. Such a RNA is commonly referred to as an antisense RNA. It has been reported that antisense RNA can interact intracellularly with its complementary sense mRNA and block the synthesis of the encoded protein (Kim and Wold Cell 1985).

pMTαB2 was used to cotransfect COS-1 cells along with the FVIII expression vector pMT2VIII using the DEAE dextran procedure. Conditioned medium was harvested at various times beginning 48 hours post-transfection and assayed for FVIII activity. The results of such an experiment are summarized in Table II. In this experiment coexpression of FVIII and antisense GRP78 sequences resulted in a 50% increase in FVIII activity in the conditioned medium compared to coexpression of FVIII and GM-CSF. This data indicates that the introduction of an antisense vector to decrease the intracellular level of GRP78 can result in increased level of FVIII secretion.

TABLE I

Cotransfection of FVIII and GRP78 Expression Vectors in COS-1 Cells

| | Chromogenic Activity (milliunits/ml) | | | |
|---|---|---|---|---|
| No DNA | 0 | 0 | 0 | 0 |
| pMT2VIII/pCSF-1 | 67 | 93 | 30 | 30 |
| pMT2VIII/pMTGRP78 | 10 | 19 | 0 | 5 |
| pMT2LA/pCSF-1 | 290 | — | 536 | 436 |
| pMT2LA/pMTGRP78 | 90 | — | 240 | 217 |

*Shown are the results of four separate experiments. The plasmids indicated were cotransfected into COS-1 cells and the conditioned medium removed for assay by the Kabi Coatest F(VIII): C method.

TABLE II

Cotransfection of F(VIII) and Antisense GRP78 Expression Vectors in COS-1 Cells

| | Chromogenic Activity (milliunits/ml) |
|---|---|
| pMTVIII/pCSF-1 | 90 |
| pMTVIII/pMTαB2 | 135 |
| No DNA | 0 |

The plasmids indicated were cotransfected into COS-1 cells and conditioned medium removed for an assay by the Kabi Coatest F(VIII): C method.

DEVELOPMENT OF CHO CELL LINES WITH REDUCED BIP/GRP78 LEVELS AND FUSION WITH FVIII PRODUCING CELL LINES (1) Development of CHO cells with reduced BiP/GRP78 levels Chinese hamster ovary (CHO) cell lines which are DHFR deficient, CHO−(DUKX-Bll), were grown in an alpha medium supplemented with 10 μg/ml each of thymidine, deoxyadenosine and adenosine. Cells were cotransfected with pMTαB2 (20 μg) and pSV2Neo (2 μg)(ATCC No. 37149) by the calcium phosphate coprecipitation procedure (Kaufman et al JMB 1982). pSV2Neo codes for resistance to the antibiotic G418 (P. Southern & Berg P. 1982 J. Mol. Appl. Genet. 1 327–341). Forty-eight hours post-transfection the cells were plated in alpha medium supplemented with nucleosides as above and including 1 mg/ml of G418 in order to select for SV2Neo expression. pMTαB2 contains an intact DHFR coding region in the 3' region of the antisense GRP78 transcript. Thus G418 resistant transformants can be subsequently selected for DHFR expression from this mRNA. Growth in alpha media lacking nucleosides with 10% dialyzed fetal calf serum resulted in DHFR+ colonies. Five colonies were pooled to produce the A6B line. This line was then amplified by selection for growth in the presence of the folic acid analogue methotrexate at a concentration of 0.02 μM.

Following approximately 8 passages in 0.02 μM methetrexate the BiP/GRP78 level in A6B was compared to CHO DUKX by immunoprecipitation of radiolabeled cell extracts with anti-BiP monoclonal and analysis by SDS PAGE. A6B showed reduced levels of BiP/GRP78 compared to the original CHO line. In addition the level of antisense GRP78 RNA derived from pMTαB2 in these cells was determined by Northern analysis.

(3) Fusion of H9 with BiP/GRP78 reduced cell line

The A6B cell line was fused with an FVIII producing cell line H9 by standard polyethylene glycol procedure following treatment of A6B with DEPC to render them nonviable (W. E. Wright, Chap 5, The Selection of Heterokaryons and Cell Hybrids Using the Biochemical Inhibitors Iodoacetamide and Diethylpyrocarbonate in Techniques in Somatic Cell Genetics, Ed. J. W. Shay, Plenum Press). Two days following cell fusion the cells were plated in 1 μM methetrexate and 1 mg/ml G418. H9 grows in 1 μM methetrexate and G418 selects for the chromosome containing the antisense GRP78 sequences derived from A6B cells. After eleven days of growth twenty-two colonies were pooled to produce the cell line designated H9xA6B-9. Determination to the level of FVIII procoagulant activity secreted into the conditioned medium by H9xA6B-9 showed that this cell line yielded two-fold greater activity than the original H9 line.

CONCLUSIONS OF BIP/GRP78 ASSOCIATION STUDY 1. wt FVIII is associated with BiP and most of the FVIII which is never secreted remains associated with BiP. 20 out of 25 N-linked glycosylation sites are clustered in middle third of the FVIII protein.

2. LA, a deleted form of FVIII which has 18 of 20 clustered glycosylation sites removed, is more efficiently secreted than wt FVIII exhibits a transient association with BiP.

3. The association of LA with BiP can be significantly increased by treatment of cells with the N-linked glycosylation inhibitor tunicamycin.

4. VWF, a complex glycoprotein which is efficiently secreted by CHO cells, exhibits only a transient association with BiP. The 17 glycosylation sites on VWF are spaced along the molecule rather than clustered as on wt FVIII.

5. tPA exhibits only a slight transient association with BiP. However inhibition of N-linked glycosylation by tunicamycin results in the intracellular retention of some of the unglycosylated molecules in a complex with BiP.

6. tPA3x, an engineered mutant of t-PA which has had three potential N-linked glycosylation sites abolished by replacement of Asn with Gln exhibits only a slight association with BiP at low expression levels. However, at high expression levels a fraction of the unprocessed protein displays a stable association with BiP and is apparently not secreted effeciently. This behavior is similar th that observed for wt t-PA when glycosylation is inhibited.

7. Intracellular retention of unglycosylated tPA in a complex with BiP is dependent on expression level. tPA3x at low expression levels is not associated with BiP and is effeciently secreted. At 200-fold higher expression levels a significant proportion of tPA3x is associated with BiP. This intracellular retention is similar to that observed for the high producer wt tPA cell line, AJ19, when N-linked glycosylation is inhibited. In a low producing wt tPA cell line, H12B, the effect of inhibition of N-linked glycosylation is less pronounced than in cells such as AJ19. This suggests that unglycosylated tPA may aggregate when present at high concentrations in the ER leading to its association with BiP.

8. BiP may associate with improperly glycosylated or folded proteins in the endoplasmic reticulum and prevent their secretion. BiP probably functions to clear aggregated proteins from the endoplasmic reticulum in an analogous function to hsp70 in heat shocked nucleoli. The problem of protein aggregation or insolubility in the ER may be exacerbated by the high expression levels now attainable by recombinant DNA expressioin techniques and for some glycoproteins such as FVIII aggregation and consequent association with BiP may prove a barrier to high level secretion.

9. The 20 clustered glycosylation sites in the middle of wt FVIII may be inefficiently glycosylated resulting in aggregation of improperly folded molecules and stable assoc'n with BiP. It is also possible that this heavily glycosylated domain assumes a conformation which BiP recognizes as aberrant even if N-linked glycosylation is appropriate. In this situation secretion competent molecules may be trapped in a complex with BiP and reduced levels of BiP may result in higher levels of secretion.

10. Reduction of BiP levels in FVIII producing cell lines results in increased secretion of FVIII acitvity into the conditioned medium. Thsu CHO cell lines with reduced levels of BiP may be of utility in the expression of certain complex glycoproteins.

1. Bole, D. G., Hendershot, L. M., and Kearney J. F. (1986) Postranslational association of immunoglobulin heavy chain binding protein with nascent heavy chains in nonsecreting and secrating hybridomas. J. Cell Biol. 102:1558–1566.

2. Lewis, M. J. and Pelham H.R.B. (1985) Involvement of ATP in the nuclear and nucleolar functions of the 70Kd heat shock protein. EMBO J. 4:3137–3143.

3. Munro, S. and Pelham H.R.B. (1986) An hsp70-like protein in the ER:identity with the 78 Kd glucose-regulated protein and immunoglobulin heavy chain binding protein. Cell 46:291–300.

4. Shiu, R. P., Pouyssegur, J., and Pasten I. (1977) Glucose deprivation accounts for the induction of two transfomation-sensitive membrane proteins in Rous sarcoma virus-transformed chick embryo fibfoblasts. Proc. Natl. Acad. Sci. U.S.A. 74:3840–3844.

5. Chappel, T. G., Welch, W. J., Schlossman, D. M., Palter, K. B., Schlesinger, M. J., and Rothman, J. E. (1986) Uncoating ATPase is a member of the 70- kD family of stress proteins. Cell 45:3–13.

6. Ungewickell, E. (1985) The 70 Kd mammalian heat shock proteins are structurally and functionally realated to the uncoating protein that releases clathrin triskelia from coated vesicles. EMBO J.4:3385–3391.

7. Pelham, H.R.B. (1986) Speculations on the functions of the major heat shock and glucose-regulated proteins. Cell 46:959–961.

8. Schlesinger, M. J. (1986) Heat shock proteins: the search for functions. J. Cell Biol. 103:321–325.

9. Williams D. B., Swiedler, S. J., and Hart, G. W. (1985) Intracellular transport of membrane glcoproteins: two closely related histocompatibility antigens differ in their rates of transit to the cell surface. J. Cell Biol. 101:725–734.

10. Lodish, H. F., Hong, N., Snider, M., Strous, G. J. (1983) Hepatoma secretory proteins migrate from rough endoplasmic reticulum to golgi at characteristic rates. Nature 304:80–83.

11. Fitting, T. and Kabat, D. (1982) Evidence for a glycoprotein signal involved in transport between subcellular organelles. J. Biol. Chem. 257:14011–14017.

12. Blobel, G. and Dobberstein, B. (1975) Transfer of proteins across membranes. II Reconstitution of functional rough microsomes from heterologous components. J. Cell Biol. 67:852–862.

13. Farquhar, M. G. (1986) Progress in unraveling pathways of golgi traffic. Ann. Rev. Cell Biol. 1:447–488.

14. Kornfeld, R. and Kornfeld, s. (1985) Assembly of asparigine-linked oligosaccharides. Ann. Rev. Biochem. 54:631–664

15. Walter, P., Gilmore, R. amd Blobel, G. (1984) Protein translocation across the endoplasmic reticulum. Cell 38:5–8.

16. Gething, M. J., McCammon, K., and Sambrook J. (1986) Expression of wild-type and mutant forms of influenza hemagglutinin: the role of folding in intracellular transport. Cell 46:939–950.

17. Sharma, S., Rogers, L., Brandsma, J., Gething, M. J., and Sambrook, J. (1985) SV40 T antigen and the exocytic pathway. EMBO J. 4:1479–1489.

18. Shiu, R. P. C., Pouyssegur, R., and Pasten, I. (1977) Glucose depletion accounts for the induction of two transformation-sensitive membrane proteins in Rous sarcoma virus-transformed chick embryo fibroblasts. Proc. Nat. Acad. Sci. U.S.A. 74, 3840–3844.

19. Haas, I. G. and Wable, m. (1983)Immunoglobulin heavy chain binding protein. Nature 306, 387–389.

20. Olden, K., Pratt, R. M., Jawosski, C., and Yamamda, K. M. (1979) Evidence for role of glycoprotein carbohydrates in membrane transport: specific inhibition by tunicamycin. Proc. Natl. Acad. Sci. U.S.A. 76, 791–795.
21. Pouyssegur, J., Shiu, R.P.C., and Pasten, I. (1977) Induction of two transformation-sensitive membrane polypeptides in normal fibriblasts by a block in glycoprotein synthesis or glucose deprivation. Cell 11, 941–947.
22. Wagner, D. D. and Marder, V. J. (1984) Biosynthesis of von Willebrand Protein by human endothelial cells: processing steps and their intracellular localization. J. Cell Biol. 99, 2123–2130.
23. Orci, L., Ravazzola, M., Amherdt, M., Madsen, O., Vassalli, J., and Perrelet, A. (1985) Direct identification of prohormone Conversion site in insulin-secreting cells. Cell 42, 671–681.
24. Pennica, D., Holmes, W., Kohr, W., Harkins, R. N., Vehar, G. A., Ward, C. A., Bennett, W. F., Yelverton, E., Seeburg, P. H., Heyneker, H., Goeddel, D. V., and Collen, D. (1983) Cloning and expression of human tissue-type plasminogen activator cDNA in E. coli. Nature 301, 214–221.
25. Kaufman, R. J., Wasley, L. C., Spiliotes, A. J., Gossels, S. D., Latt, S., A., Larsen, G. R., and Kay, R. M. (1985) Coamplification and coexpression of human tissue-type plasminogen activator and murine dihydrofolate reductase sequences in Chinese hamster ovary cells. Mol. Cell Biol. 5, 1750–1759.
26. Toole, J. J., Pittman, D. D., Orr, E. C., Murtha, P., Wasley, L. C., and Kaufman, R. J. (1986) A large region (95 kDa) of human factor VIII is dispensible for in vitro procoagulant activity. Proc. Natl. Acad. Sci. U.S.A. 83, 5939–5942.
27. Laemmli, U. K. (1970) Cleavage of structural proteins during the assembly of the head of bacteriophage T4. Nature 227, 680–685.
28. Toole, J. J., Knopf, J. L., Wozney, J. M., Sultzman, L. A., Buecker, J. L., Pittman, D. D., Kaufman, R. J., Brown, E., Shoemaker, C., Orr, E. C., Amphlett, G. W., Foster, W. B., Coe, M. L., Knutson, G. J., Fass, D. N., and Hewick, R. M. (1984) Molecular cloning of a cDNA encoding human antihaemophilic factor. Nature 312, 342–347.
29. Gibson, R., Schlesinger, S., and Kornfeld, S. (1979) The nonglycosylated glycoprotein of vesicular stomatitus virus is temperature-sensitive and undergoes intracellular aggregation at elevated temperatures. J. Biol. Chem. 254, 3600–3607.
30. Gibson, R., Kornfeld, S., and Schlesinger, S. (1981) The effect of oligosaccharide chains of different sizes on the maturation and physical properties of the G protein of vesicular stomatitis virus. J. Biol. Chem. 256, 456–462.
31. Takasuki, A., Kohno, K., amd Tamura, G. (1975) Inhibition of biosynthesis of polyisoprenol sugars in chick embryo microsomes by tunicamycin. Agric. Biol. Chem. 39, 2089–2091.
32. Bonthron, D. T., Handin, R. I., Kaufman, R. J., Wasley, L. C., Orr, E. C., Mitsock, L. M., Ewenstein, B., Loscalzo, J., Ginsburg, D., Orkin, S. H. (1986) Structure of pre-pro-von Willebrand factor and its expression in heterologous cells. Nature 324, 270–273.
33. Pohl, G., Kallstrom, M., Bergsdorf, N., Wallen, P., and Jornvall, H. (1984) Tissue plasminogen activator: peptide analysis confirm an indirectly derived amino acid sequence, identify the active site serine residue, establish glycosylation sites, and localize variant differences. Biochemistry 23, 3701–3707.

What is claimed is:

1. An anti-sense expression vector capable of directing the transcription in a host cell of mRNA complementary to mRNA encoding the host cell's GRP78, said vector comprising a DNA sequence encoding host cell GRP78 peptide sequence operatively linked to an expression control sequence in reverse orientation such that transcription of the DNA produces the anti-sense mRNA.

2. A eucaryotic host cell for expressing a protein heterologous to the cell which comprises a host cell transformed with a vector of claim 1.

3. A yeast, fungal, insect, plant or mammalian host cell of claim 2.

4. A host cell of claim 2 which is additionally transformed with a vector capable of directing the expression of a protein heterologous to the cell.

5. A host cell of claim 4, wherein the protein heterologous to the cell is a factor VIII protein.

6. A method for producing a protein heterologous to a host cell by culturing a host cell transformed with a vector capable of directing the expression of the heterologous protein, the improvement comprising culturing a transformed host cell of claim 4 as the transformed host cell.

7. A method for producing a factor VIII protein which comprises culturing the improved host cell of claim 5 and recovering from the culture medium the Factor VIII protein so produced and secreted.

* * * * *